(12) United States Patent
Smith et al.

(10) Patent No.: US 10,706,372 B1
(45) Date of Patent: *Jul. 7, 2020

(54) VALUE OF FUTURE ADHERENCE

(71) Applicant: RXANTE, INC., Portland, ME (US)

(72) Inventors: Daniel Smith, McLean, VA (US);
Joshua Benner, McLean, VA (US);
Aaron McKethan, McLean, VA (US);
Loren Lidsky, McLean, VA (US)

(73) Assignee: RXANTE, INC., Portland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/416,397

(22) Filed: May 20, 2019

Related U.S. Application Data

(63) Continuation of application No. 14/519,557, filed on Oct. 21, 2014, now Pat. No. 10,318,897.

(60) Provisional application No. 61/893,750, filed on Oct. 21, 2013.

(51) Int. Cl.
*G06Q 50/22* (2018.01)
*G06Q 10/06* (2012.01)

(52) U.S. Cl.
CPC ......... *G06Q 10/0631* (2013.01); *G06Q 50/22* (2013.01)

(58) Field of Classification Search
CPC .... G06Q 40/00; G06Q 50/00; G06Q 10/0631; G06F 7/00
See application file for complete search history.

(56) References Cited

U.S. PATENT DOCUMENTS

| 8,639,622 | B1 | 1/2014 | Moore | |
|---|---|---|---|---|
| 2004/0049506 | A1 | 3/2004 | Ghouri | |
| 2009/0089084 | A1 | 4/2009 | Schoenberg | |
| 2010/0205008 | A1* | 8/2010 | Hua | G06F 19/3456 705/3 |
| 2012/0179481 | A1* | 7/2012 | Patel | G06Q 30/02 705/2 |

* cited by examiner

*Primary Examiner* — Jonathan Durant
*Assistant Examiner* — Chad A Newton
(74) *Attorney, Agent, or Firm* — Nixon & Vanderhye, P.C.

(57) ABSTRACT

The present technology calculates a value of future adherence (VFA) score which is a patient-level, predicted, expected cost of conversion from non-adherence to adherence over a specified time-frame. The score consists of three general components: (1) probability of being non-adherent, (2) cost reduction associated with being adherent, and (3) probability of converting from non-adherent to adherent. These values can be combined to create an overall VFA score. A user interface is then provided which shows at least a list of patients and information related to the VFA score.

20 Claims, 9 Drawing Sheets

| PID | NAME | ... | PROBABILITY OF NON-ADHERENCE | PROBABILITY OF CONVERSION | COST REDUCTION WHEN ADHERENT | VFA SCORE |
|---|---|---|---|---|---|---|
| 1 | Armstrong, Jane | ... | 0.7233 | 0.050 | $2,371.00 | 85.7 |
| 2 | Armstrong, John | ... | 0.6531 | 0.100 | $1,428.57 | 93.3 |
| ... | ... | ... | ... | ... | ... | ... |
| n | Bradsher, Joan | ... | 0.6837 | 0.050 | $2,384.09 | 81.5 |

FIG. 3

VALUE OF FUTURE ADHERENCE

CROSS-REFERENCES TO RELATED APPLICATIONS

This application is a continuation of U.S. patent application Ser. No. 14/519,557 filed Oct. 21, 2014 which claims priority to U.S. Patent Application No. 61/893,750 filed Oct. 21, 2013. The entire contents of each of these applications are incorporated herein by reference.

BACKGROUND AND SUMMARY

The health care profession is rapidly changing. We now live in a time where health care has become a daily discussion for most media outlets. It is now more important than ever for health care providers, health insurance companies, and health care facilities to understand the costs associated with each patient and the patient's adherence (or non-adherence) to a treatment program.

Health care has become an increasingly popular topic these days, especially in light of recent legislation enabling the public greater access to health care. Certain technology has enabled health care providers the ability to monitor the adherence level for each patient to a particular health care therapy (e.g., adherence to a drug regimen), and use such data to advance the practice of the particular health care provider. Certain techniques are described in related U.S. application Ser. Nos. 13/729,817 and 14/319,450, each of which are incorporated herein by reference.

Conventional technology related to monitoring adherence to a particular health care regimen is helpful in that it can convey how involved a patient is when participating in a particular therapy. However, such technology does not necessarily convey to a health care provider the actual value associated with potential future adherence to a particular therapy. In particular, such technology does not create a metric for conveying to a health care provider the probability related a patient for the adherence (or non-adherence) to a therapy taking into account the probability of the patient converting to being adherent (e.g., from being non-adherent) and the potential cost reduction associated with becoming adherent.

BRIEF DESCRIPTION OF THE DRAWINGS

FIG. 3 is an illustrative table showing scores and values.

DETAILED DESCRIPTION OF THE TECHNOLOGY

Figure 1:
FIG. 1 shows a non-limiting example user interface.

The present technology relates to health care and health care data analytics. The technology estimates the total opportunity of cost avoidance for a patient population resulting from non-adherence and creates the means for prioritizing patients based on their individual Value of Future Adherence (VFA) score. The technology further facilitates efficient population-level improvements in medication adherence and other health care outcomes.

The technology relates to analytics platform having an iterative data process comprising a) prediction, b) patient selection/prioritization, c) and evaluation analytics to continuously optimize performance on medication quality indicators at a population level, including medication adherence. The technology uses patients' predicted future medication outcomes, other patient characteristics derived from patient data, and intervention capacity attributes to compute the most cost-effective intervention recommendation for each individual patient on a recurring basis based on accumulating data.

Conventional technology is capable of calculating cost differences between an adherent population and a non-adherent population. For example, there exists a methodology where static, population-level cost differences are multiplied by prevalence of disease figures to estimate a population-level opportunity cost. But the technology considers cost estimates only and not patient-level probabilities of non-adherence or the likelihood of conversion from non-adherence to adherence. As such, overall population-level estimates are highly inaccurate/over-stated and, importantly, there is no differentiation at the patient-level. Patient-level cost differentiation facilitates comparisons to be made to intervention costs allowing for strategic targeting. Furthermore, many of the conventional systems fail to provide any metric for measuring the value associated with a patient's future adherence to a treatment plan. Thus, there is a need for a system that can determine such patient-level cost differentiation taking into account the drawbacks of the present technology.

The present technology calculates a VFA score which is a patient-level, predicted, expected cost of conversion from non-adherence to adherence over a specified time-frame. The score consists of some general components including, but not limited to: (1) probability of being non-adherent, (2) cost reduction associated with being adherent, and (3) probability of converting from non-adherent to adherent. In particular, the score takes into account the probability that a patient will be non-adherent to a therapy, a probability that the patient will convert to becoming adherent, and a cost value associated with the cost reduction from being adherent as opposed to being non-adherent. The VFA score thus provides a metric for a health care provider, for example, to determine the most cost-effective intervention recommendation for each individual patient (particularly on a recurring basis based on accumulating data). Thus, patients VFA scores can be conveyed to a health care provider (e.g., via a user interface) in order for the provider to accurately determine the value associated with recommending intervention for a patient (e.g., to help the patient become more adherent to a therapy).

In determining the VFA, the cost component for each patient may be calculated (1) using data elements available at the time of prediction on pharmacy administrative claims data to select a figure from a pre-calculated cost table and/or (2) using medical claims to forecast patient-level cost. The pre-calculated cost table is a table of cost differences between a population adherent to a particular therapy area (class of drugs) or disease-state set of drugs, and a non-adherent population. The table is stratified by characteristics that are available on pharmacy administrative claims data so that values found on a claim may be used to select, or 'look up,' a cost value in the table particular to each stratification.

As a non-limiting example, the table can be constructed by considering any demographic or clinical characteristics that are available on pharmacy claims data as stratification variables. Each potential stratification variable (or combination of variables) is tested and dynamically selected via a series of cost models. The stratification selected for a therapy area is the set of variables that exhibits the best combination of strong interaction effect and small standard errors. This combination provides information for the cost table that yields the best cost forecasts. The table may be constructed from an existing dataset of medical administrative claims data or derived from, and therefore customized to, a client's medical claims dataset. This allows for more accurate cost component estimates even when medical data are not available.

The probability of converting from non-adherent to adherent may be set according to scenario testing. For example, a conservative probability would be 5% where an extreme probability would be 100%. The probability of converting from non-adherent to adherent may also be set through factors related to the probability of non-adherence component of the VFA score. Such scores reflect different behaviors, or the likelihood, of transitioning from a non-adherent state to an adherent state.

The VFA score can be calculated by multiplying the three components. It should be appreciated that the score can combine the components in any mathematical fashion and is not limited to only multiplying the components together. The calculated VFA score can serve as a metric for conveying (e.g., to a health care provider) the value associated with potential future adherence to a selected therapy.

The technology described herein can be used to create both a member-level and population-level estimate of cost avoidance due to non-adherence. Population estimates created with the VFA score are more accurate than methods that do not account for likelihood of being non-adherent in future or the likelihood of conversion from non-adherent to adherent. Further, patient-level estimates allow for strategic intervention targeting which is not possible with static population-level cost differences. Finally, each component of the VFA score includes at least a probability of being non-adherent, a cost reduction associated with being adherent, and a probability of converting from non-adherent to adherent is calculated using a sophisticated approach, yielding the best known estimates.

FIG. 1 shows a non-limiting example user interface for a system that can convey the VFA score for each patient for a particular practice. FIG. 1 shows general "welcome" information for introducing the user to the system. The user can select one or more practices to view their patient population based on practice ID PRID. In this example, the John Smith Medical Group is selected to view the relevant patient population as well as the VFA score associated with each patient.

Figure 2:
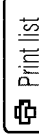
FIG. 2 shows a non-limiting example user interface.

FIG. 2 shows an example interface for displaying a list of patients with their associated therapies where each patient is shown with their medication adherence PMA, VFA Score VFA, and Intervention Recommendation IR. The interface shows the patients for a particular practitioner PRID where each patient is listed with a patient identification PID (e.g., the patient's first and last name) The patient ID can also include the patient's date of birth as well as any other particular identification information for the patient (e.g., social security number, insurance ID, driver's license number).

In the example shown in FIG. 2, each patient ID is listed in alphabetical order based on the name of the patient. For each patient, the interface can show the patient medication adherence PMA, a VFA Score VFA, and/or an Intervention Recommendation IR for each patient PID. The patient medication adherence PMA shows how adherent a patient is to a therapy for treating a particular condition. That is, the PMA is a variable showing recent history that can have an impact on the overall adherence score for the patient. For example, patient "Jane Armstrong" is shown having a health condition ID CID of "blood pressure" in which the patient is taking a certain drug regimen to treat the blood pressure condition. The interface can show the days past (or days until) the next refill date RD. In this example, 5 days have passed between the current date and the date that "Jane Armstrong" prescription should have been refilled. For example, "Jane Armstrong" may have had a next refill date of May 1, 2014 where the current date could be May 6, 2014.

The display can also be adjusted so that the patients are prioritized and/or ordered based on the number of medications/therapies they are engaged. For example, "Mike Armstrong" could be listed at the top as he has multiple therapies (e.g., blood pressure and cholesterol). The system could also eliminate practices that do not have a high enough patient participation number.

As discussed above, many systems that monitor therapy adherence for patients of a particular practice lack the ability to convey an easy-to-understand metric for determining the value associated with recommending intervention for a patient. While certain technologies can show the score related to the probability of a patient being adherent, or show the cost associated when the patient becomes adherent, these systems fail to provide a useful metric for assigning a value to the adherence of a particular patient. For example, in certain instances, a patient may have a relatively high cost reduction associated with adherence, yet the probability of converting the patient to being adherent may be extremely low. Likewise, a patient may have a relatively average cost reduction associated with adherence, but have a higher probability of converting from non-adherence to adherence. Thus, the VFA score provides a metric for enabling a party (e.g., a health care provider) to understand the overall value associated with a patient's adherence, especially for determining if it is worthwhile for the provider to recommend intervention. For example, the VFA score can quantify the combination of (a) the probability that a patient will not be adherent, (b) a probability of converting a patient from non-adherent to adherent, and (c) a cost reduction associated when converted. This score provides an easy-to-understand value showing which patients would be the most valuable in recommending intervention. This can be useful especially for providers that have a large patient population and cannot spend the time and/or resources involved in recommending or conducting interventions for each patient.

In the example shown in FIG. 2, the VFA score for each patient is shown and, based on the VFA score, an Intervention Recommendation IR for suggesting whether it would be worthwhile for the provider to suggest intervention. In the example shown in FIG. 2, both Mike Armstrong and John Armstrong have indicators showing a recommendation for intervention as both patients have relatively higher VFA scores at $93.30 and $97.40, respectively. The system can apply a variety of factors in determining whether intervention should be recommended. For example, a threshold could be established recommending intervention when a patient's VFA exceeds a certain value (e.g., $90.00). Likewise, the system could be configured to select a certain percentage of patients with the highest VFA score compared to other patients. Of course, these examples are non-limiting and a variety of different factors and techniques can be used in determining whether to recommend intervention.

As discussed above, the VFA score conveys to a user the associated value related to the most cost-effective intervention recommendation for each individual patient. For example, Jane Armstrong has a relatively high VFA score of $85.70. This could reflect that Jane Armstrong has a high cost reduction associated with converting from being non-adherent to adherent. Likewise, the score could also reflect that Jane Armstrong has a relatively higher probability of conversion. The score could also reflect that Jane Armstrong has a higher probability of being non-adherent. The VFA score helps make such factors more transparent by providing an easy-to-understand metric for determining the associated value with a recommended intervention. Thus, a user (or health care provider) would understand that the associated VFA score of $85.70 with Jane Armstrong shows that the value associated with intervention may be relatively higher than other patients. The interface shown in FIG. 2 thus advantageously conveys the VFA score for each patient so that a user/provider can determine which patients would be more valuable in recommending interventions compared to others.

It should be appreciated that the interface shown in FIG. 2 is non-limiting and can include any variety of additional components. For example, the display could be modified to show the cost associated with performing an intervention. Such information would be useful in balancing the cost against a particular VFA score. For example, if Jane Armstrong has a $100 cost associated with intervention, a provider would be unlikely to recommend intervention as it would not even cover the VFA score of $85.70. That is, the value associated with intervention would be less than the overall cost involved in the intervention. Of course, this example is non-limiting and the display in FIG. 2 could be modified to show a variety of different components.

It should also be appreciated that the VFA score for each patient could be used to guide a user to an appropriate intervention for a particular patient. That is, a user could have a variety of intervention options available to them including, but not limited to, a call center, sending a letter, sending a text message, sending an email, and/or generating an automated voice call. The VFA score could be used to weigh the value of the intervention against the cost of a particular intervention. For example, a patient could have a VFA score of $95 for a particular therapy where five intervention options may be available. One intervention may cost $75 where the other four interventions may cost $100. Thus, a user could select the intervention costing $75 as that is the only intervention below the value of the score thereby giving the user one clear intervention choice.

The VFA score could be used to balance the cost of intervention selected against the value of intervention. That is, by sorting an individual by the VFA score, the user has the ability to select the population that is appropriate for adherence intervention. Thus, the user can weigh different factors in selecting a particular intervention, including the cost of the intervention and the overall effectiveness. As such, although some interventions may have higher costs than others, showing the cost of the intervention relative to the VFA score may incentivize the user to select a higher costing intervention as the likelihood of the intervention will have a better chance of the patient becoming adherent. That is, the VFA score overall blends several characteristics that make it easier for a user to compare costs (e.g., relative to the cost of a particular intervention).

A user may also have a total budget for interventions that may also be shown to the user via the display. When an intervention is selected, the overall budget may be reduced by the selected intervention. Thus the system could advantageously allow the user to choose the most cost effective interventions while knowing their available budget.

It should be appreciated that the display shown in FIG. 2, for example, could be modified to show the different options available for intervention. Likewise, the display could additionally show the cost associated with each particular intervention so that a user can best understand which interventions will be most cost effective relative to the value of the intervention (e.g., as shown in the VFA score). This information could be displayed in an extra column, shown as a pop-up box, or displayed via some selectable item (e.g., radio button, drop-down menu, check box). By displaying the cost associated with the intervention in combination with the patient's VFA score, the user can effectively "draw a line" when it comes to investing in a particular intervention. That is, the user can demarcate which intervention options would be too costly (or not effective) with options that would be most cost effective.

FIG. 3 is an illustrative table 1 showing the VFA score and values associated with calculating the VFA score for each patient. The table 1 can be displayed on a display and can be integrated for use with a user interface. In the table 1, the VFA score for each patient can be calculated. For example, each patient could be associated with a patient ID PID where several pieces of information including, but not limited to, the name, gender, and/or other demographic information are associated with the patient.

In the example shown in FIG. 3, the table 1 contains a list of patients with patient ID PID, the patient name, the respective patient's probability of non-adherence, probability of converting from being non-adherent to adherent, the cost reduction associated when the patient is adherent (e.g., the cost of being non-adherent minus the cost of being adherent), and the resultant VFA score associated with these variables. Although the example interface shown in FIG. 2 displays only the VFA score, the interface could also be modified to include at least the information provided in table 1. Such information could provide further details as to the exact variables used to calculate the VFA score.

As can be seen in this example, John Armstrong has a higher VFA score due to a higher probability of conversion even though his cost reduction associated with adherence is lower than the other displayed patients. Likewise, Joan Bradsher has a lower VFA score than Jane Armstrong even though both patients have relatively similar cost reductions associated with being adherent and the same probability of conversion. This is due, in part, to Joan Bradsher having a lower probability of being non-adherent than Jane Armstrong. As a non-limiting example, such a lower probability could be indicative of Joan Bradsher being more likely to adhere to a particular therapy than Jane Armstrong thus resulting in a lower VFA score. That is, the lower VFA score tells a user that it would be less beneficial to attempt intervention with Joan Bradsher when compared to Jane Armstrong because Joan Bradsher would potentially have a higher likelihood of becoming adherent on her own.

FIGS. 4A-D show illustrative flowcharts for deriving a value of future adherence. The system begins by identifying a list of one or more patients for calculating a value of future adherence (S1). This list can be determined using one or more pre-periods that include claims data (e.g., health care claims data) in each period. For example, a first pre-period (pre-period 1) could be reflective of the health history of a patient starting from today and going back 90 days (e.g., the last 3 months of health history from the current date). A second pre-period (pre-period 2) could be reflective of any time outside of the past 90 day window including, but not limited to, all health care claim history beyond 90 days. For identifying members on a particular therapy the system uses, as a non-limiting example, the health care related claims from pre-period 2 (e.g., outside of the last 90 days). Candidates with a claim for a therapy of interest are considered on a therapy and are candidates for a VFA score.

Upon creating the list of patients, the system can obtain/calculate a probability score of non-adherence for each patient (S2). The probability score could be the probability of non-adherence for a particular patient. For example, a patient could have a probably score of 45 which could indicate that there is a 45% chance the patient will not be adherent to their medical treatment, which could include taking medications.

Figure 4A:
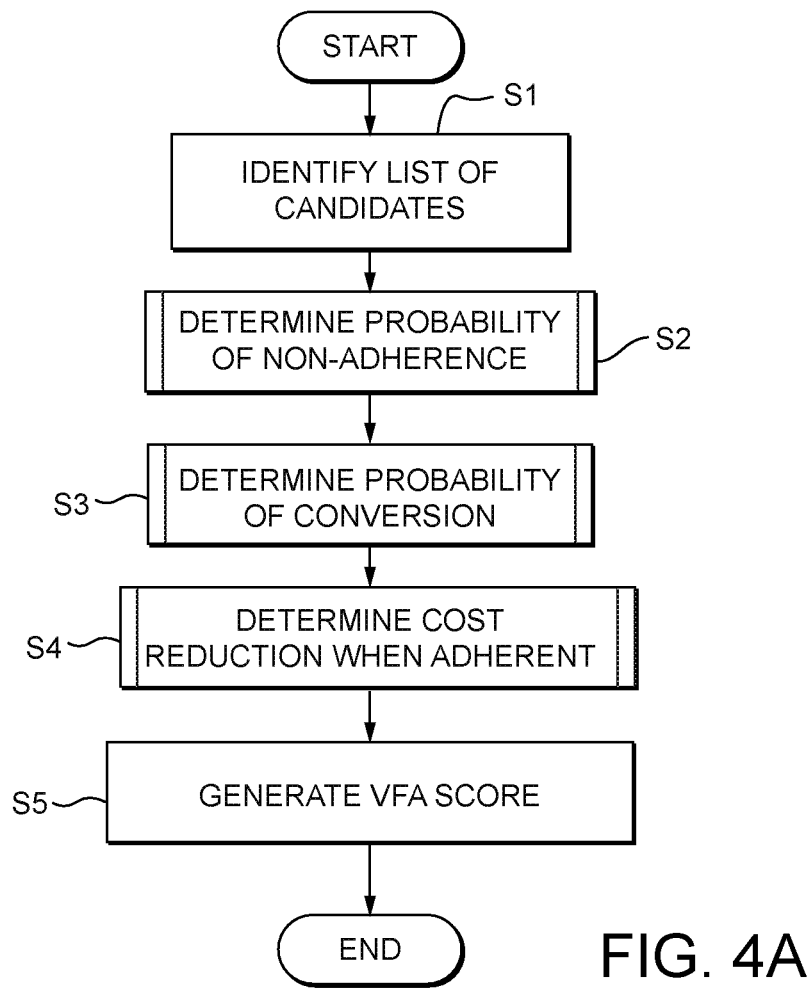
FIGS. 4A-D show illustrative flowcharts.
Figure 4B:
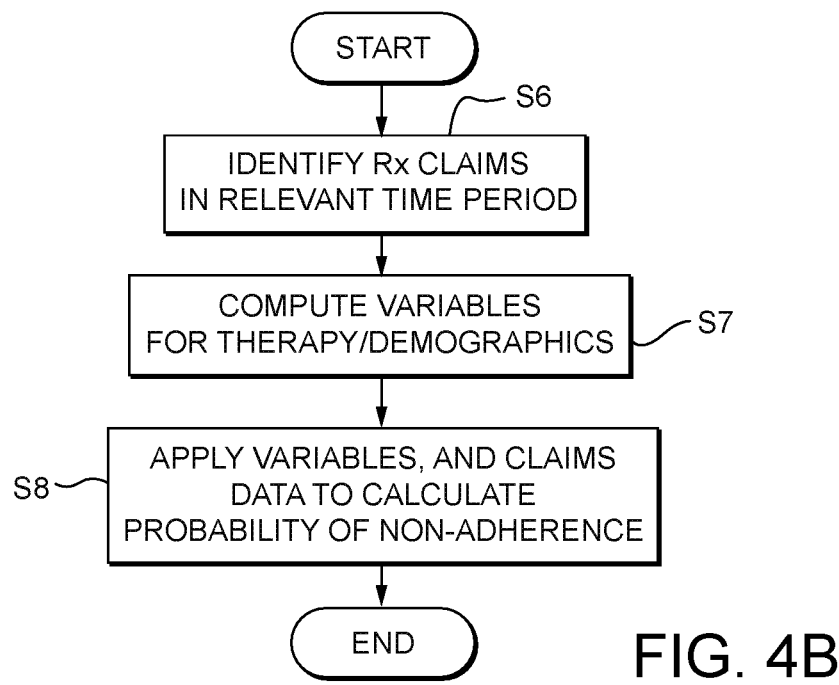

FIG. 4b shows further details regarding the calculation involved in determining the probability of non-adherence. The system can first identify health care claims in the relevant time period (S6). In this example, the health care claims for determining the probability of non-adherence can be taken from claims in pre-period 1 (e.g., the claims within the last 90 days). The system then computes variables related to the therapies as well as any relevant demographic variables (S7). For example, variables related to a therapy of interest, variables related to other therapies (e.g., peripheral therapies), and demographic variables regarding the candidate/patient can be computed. This information is combined with a predictive model to determine the overall probability of non-adherence for a particular candidate/patient (S8).

Figure 4C:
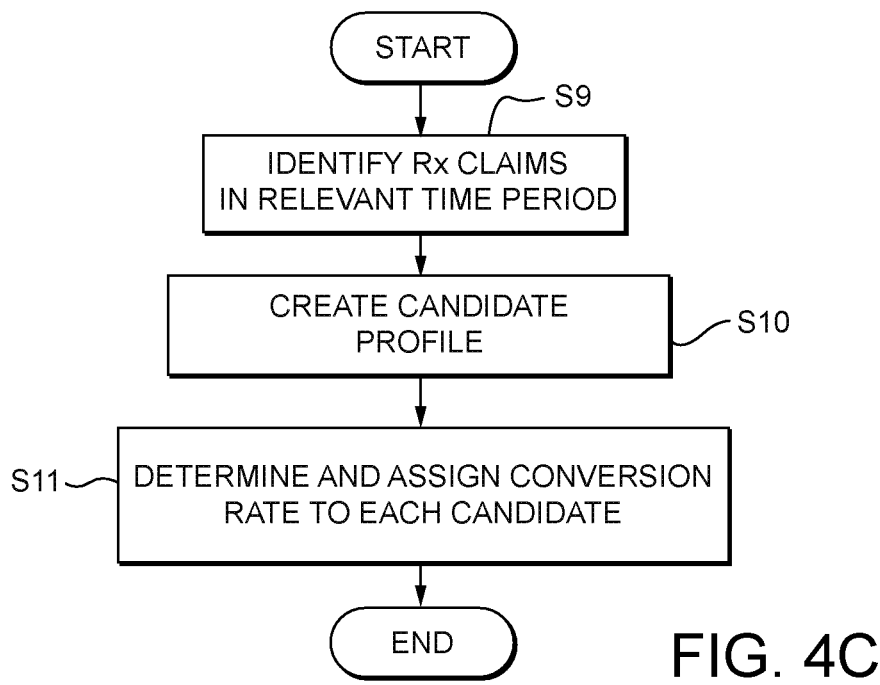

Upon calculating the probability score for each patient, the system can then determine the probability of converting a patient from being non-adherent to adherent (S3). FIG. 4c describes a non-limiting flow of processes for determining the probability of converting a patient from non-adherence to adherence. The system can identify the health care claims in a relevant time period (S9) which, in this example, would be pre-period 1. Upon determining the therapy claims for the patient, the system can create a profile for each member based on relevant characteristics determined from evaluation experience (S10). For example, the system could use information and results from previous outreach research (e.g., evaluation of outreach effectiveness) in creating the profile. Of course, it should be appreciated that other factors may be used (e.g., age, gender, acuity) as well as other models to determine the probability of conversion, and the rate may vary by an outreach type. The system can assign a conversion rate to each member in their respective profile and look up the conversion rate using the associated profile (S11). The result will be a rate of conversion for each candidate/patient that can be used as a component for calculating the VFA score.

Figure 4D:
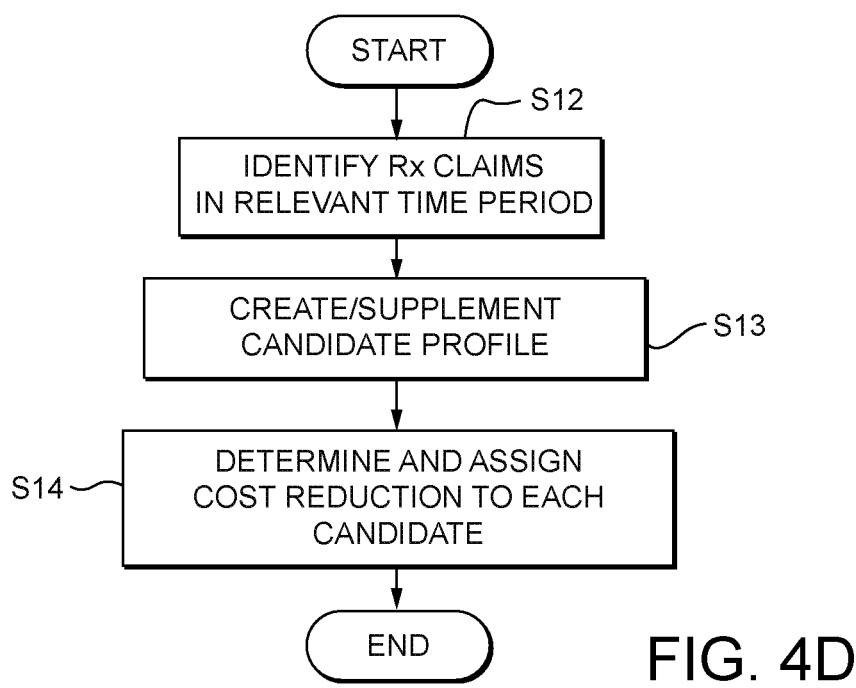

The system can analyze the medical condition and/or medical history of the patient to help determine factors in calculating the cost reduction value associated with the patient becoming adherent as opposed to being non-adherent (S4). FIG. 4d shows a non-limiting example flow of processes for determining the cost reduction associated with being adherent. The system can again identify health care claims for a patient within a relevant time period (S12) which, in this example, are claims in pre-period 1. The system can then create (or update) a profile for the patient based on relevant characteristics (e.g., found on health care/drug claims data) (S13). The profile could be created/modified based on various research and modeling factors. Upon creating/modifying the profile, the system can determine and assign a cost reduction to each candidate and reference such information by using the profile of the candidate (S14). The cost reduction could be calculated by subtracting the cost of adherence from the cost of non-adherence (or some other statistical method could be employed). That is, the system can determine the cost associated with being non-adherent and then subtract the cost associated with being adherent for a particular candidate. This value would yield the overall cost associated with converting from being non-adherent to adherent.

Upon determining (a) the probability of being non-adherent, (b) the probability of converting from non-adherence to adherence, and (c) the cost reduction associated with adherence, the system can calculate the VFA score for each candidate/patient (S5). As a non-limiting example, these factors will be combined in some fashion (e.g., mathematically combined) to yield the VFA score. For example, the factors can be multiplied together to yield the VFA score for each patient/candidate. Using the example of Jane Armstrong in FIG. 3, the probability of non-adherence (0.7233) is multiplied by the probability of conversion (0.050) which is then multiplied by the cost reduction associated with adherence ($2,371.00) yielding the VFA score of $85.70. As explained above, the VFA score will advantageously reflect the overall value in recommending an intervention for a particular patient.

Figure 5:
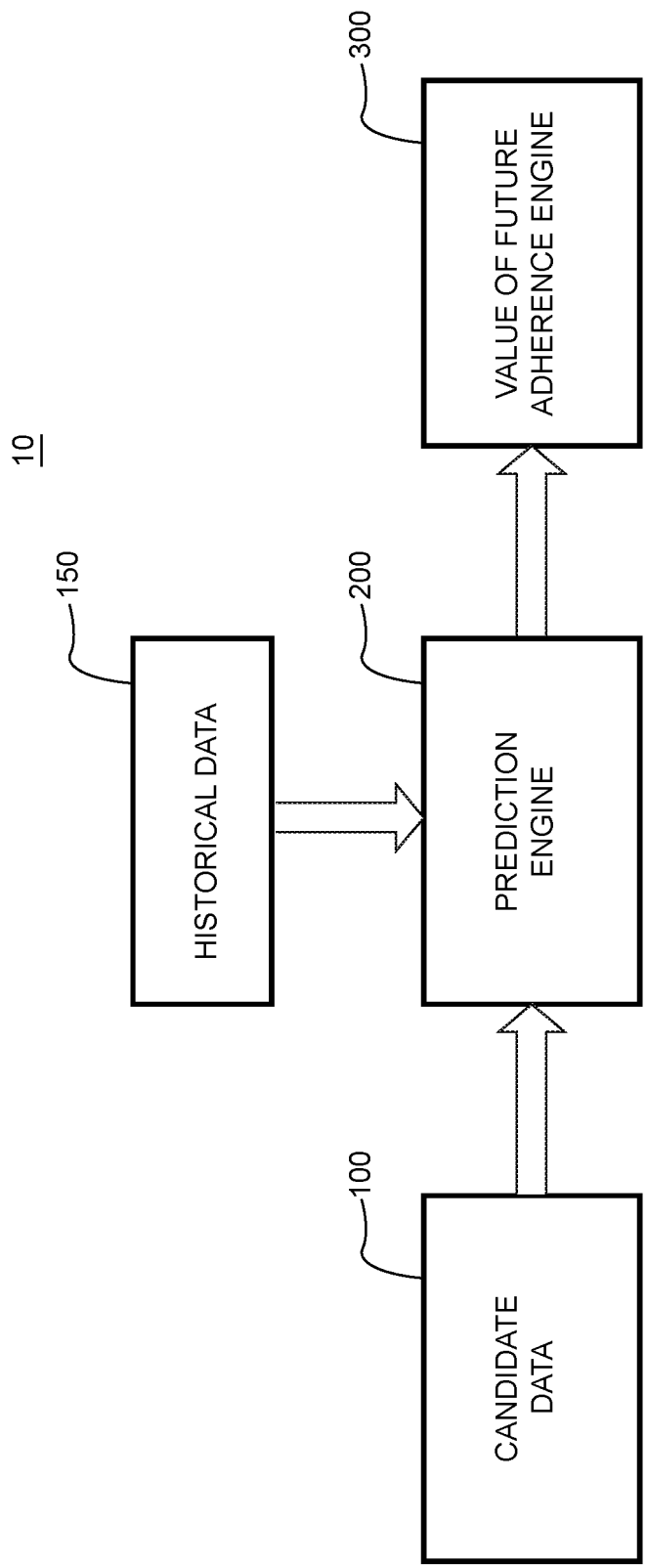
FIG. 5 is an illustrative block diagram showing elements of an example embodiment.

FIG. 5 is an illustrative block diagram showing elements of an example embodiment. The basic elements 10 are described very generally with respect to FIG. 5 and will be described in further detail below with respect to the remaining drawings. The system includes, for example, candidate patient data 100, which is processed as described herein and provided to a prediction engine 200. The prediction engine 200 is developed as described below and includes development of a prediction function which is based, at least in part, on an analysis of historical patient data 150 which may include historical data on intervention performance (for example, and without limitation, tracking data). When the prediction function of the prediction engine 200 is applied to the candidate patient data 100, a tailored patient-specific score is output and can be provided to a value of future adherence engine 300.

Figure 6:
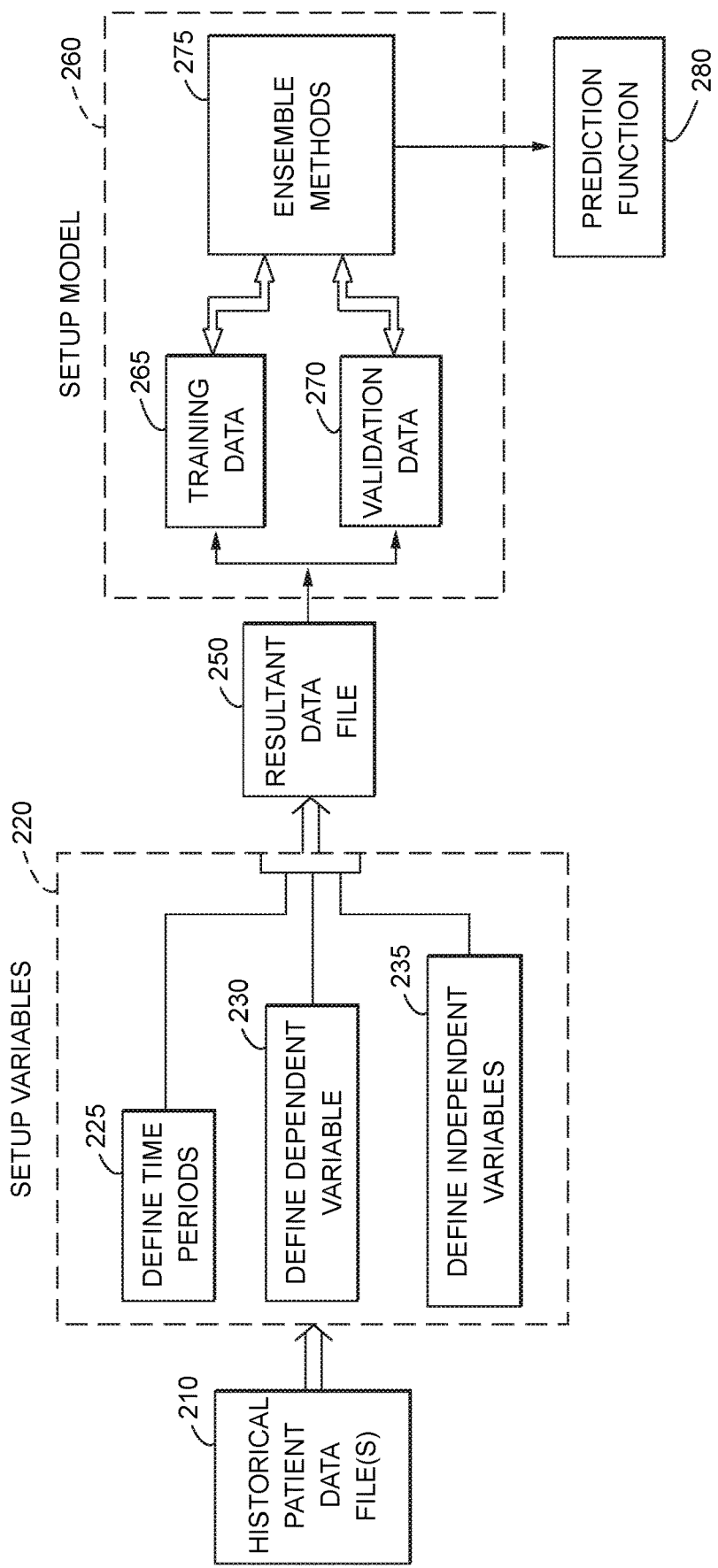
FIG. 6 shows an illustrative block diagram of an example setup procedure in accordance with an example embodiment.

FIG. 6 shows an illustrative block diagram of an example setup procedure used to define a prediction function in accordance with an example embodiment. As illustrated in FIG. 6, historical patient data 210, which may be in the form of a retrospective data file (or multiple files) from the implementation entity or program sponsor, is provided. Data in these files may include, for example, demographic, survey, clinical and/or administrative claims data about patients who would have been candidates for the adherence program, plus filled prescriptions data to allow for calculation of actual adherence after initiation of the medication therapy of interest. It will be understood that the data sources may vary and may include other example data, such as, for example, administrative claims, electronic medical records, lab results, patient surveys, socio-demographic detail, consumer purchasing data, etc. It will also be understood that different and multiple sources of data may be used to determine any number of independent variables for use in developing the predictive function described below.

The historical patient data 210 is analyzed and used during setup 220 to define certain variables 225, 230 and 235, for example, which may be used to determine a prediction function 280. For example, certain time periods 225 may be defined to assist in the extraction of various variables. Time periods of interest 225 may include, for example, an inception window or range of dates between filled prescriptions for the target medication which may be used to identify candidate patients for the adherence program. An index date for each patient which reflects the date of the first filled prescription for the target medication during the inception window may also be defined. It may also be useful to define a look back period during which the pre-index information is collected about each patient. A common example look back period is one year, but it will be understood that the look back period can range from zero days to many years. In addition, a follow-up period may be defined. A common follow-up period may typically be one year, but the follow-up period may range from one day to many years.

It is next preferable to define a dependent variable 230, sometimes also referred to as the measure to be predicted. In the medication adherence example, a common measure of medication adherence is the binary outcome of a proportion of days covered being greater than or equal to eighty percent. In other words, this dependent variable 230 would be satisfied if the patient obtained sufficient prescriptions to have the medication on hand for at least eighty percent of the days in the follow-up period. It will be understood that definitions of adherence may vary and that the definition set forth above made by way of illustrative non-limiting example. Other examples may include, proportion of days covered, medication possession ratio, discontinuation, etc. Additionally, threshold values may likewise vary, e.g., >=80%; >=70%; >=60%, etc. With the dependent variable 230 defined, it may then be useful to define a number of independent variables 235.

Independent variables 235, may be developed based on published studies of factors associated with adherence in a particular therapy area. These may, for example, fall into three broad category areas. One broad category area may be, for example, attributes of the patient, e.g., age, sex, county of residence, health status and prior health care utilization. Another broad category may include, for example, attributes of the target drug regimen, e.g., specific drug, strength, quantity dispensed, cost, etc. A third broad category may include, for example, attributes of the health care system, e.g., prescriber's specialty, number of pharmacies used, health plan design, etc.

Independent variables 235 may include variables known to be predictive of adherence and may include variables not known to be associated with adherence, but which can be rapidly tested using data mining methods to derive these from the patient data itself. For example, software running on a computer system may be used to automatically create independent variables. These variables generally may relate to the presence/absence and frequency of all possible drugs, diagnoses and procedures in the patient look-back period. Survey data may also be included in the provided data and all possible responses may also be included. It will be understood that different and multiple sources of data may be used to determine any number of independent variables for use in developing the predictive function.

A resultant data file 250 is generated to include the setup variables 220 that are generated as described above. Patient data files may be augmented and restructured to provide a common data structure for the resultant data file 250 in order to more efficiently process the data contained in the resultant data file 250. The resultant data file includes information for each patient of interest from the historical patient data files 210 and include the setup variables 220 discussed above.

Once the resultant data file 250 is created, it is provided to a further model setup procedure 260, that will result in a prediction function 280 that is then applied to candidate data to produce a patient-specific score, in this case an adherence score. Creation of the prediction function 280 is discussed in more detail herein. In general, the resultant data file is analyzed using multiple statistical methods to develop the best predictive function when tested and validated against the historical patient data in view of the fact that actual adherence can be determined with respect to the historical patient data. As a specific example, the resultant data file 250 may be divided into two parts, a "training" data file 265 and a "validation" data file 270. The system may then use, for example, multiple statistical methods 275, including, for example, any one or more of the following: logistic regression, random forests, classification and regression trees (CART), stacking, boosting, or the like, on the training data 265. These statistical methods may generally be combined, and as such, be referred to as ensemble methods 275 for determining or creating a model or predictive function based on the training data 265 that will yield highly predictive results. For example, as noted above, the resultant data file 250 may be partitioned into two parts, the "training" data 265 and the "validation" data 270 as described above. For the purposes of example, the resultant data may be randomly partitioned so that eighty percent (80%) are the "training" data 265 and the remaining twenty percent (20%) of the resultant data are in the "validation" data 270 set. It will be understood that any statistically proper partitioning may be selected based on the type of analysis and regression to be applied to the data. The models or predictive functions are developed and tested using the training data 265 over multiple statistical methods as discussed above (e.g., ensemble methods), and then testing the predictive function against the validation data 270, which is also commonly referred to as held-out data. A predictive function that is derived from the training data 265 may then be applied to the validation data 270, and the predictive function that is determined to perform best on the validation data 270 is selected as the predictive function to be applied to the candidate patient data as described below. It will be understood that any number of other possible statistical methods may be used to generate the resulting prediction function, and that the system and method disclosed is not limited to the particular example statistical methods described herein. In this manner, the independent variables or predictors are used to predict the dependent variable using the predictive function 280 created on the basis of the historical patient data 210.

Figure 7:
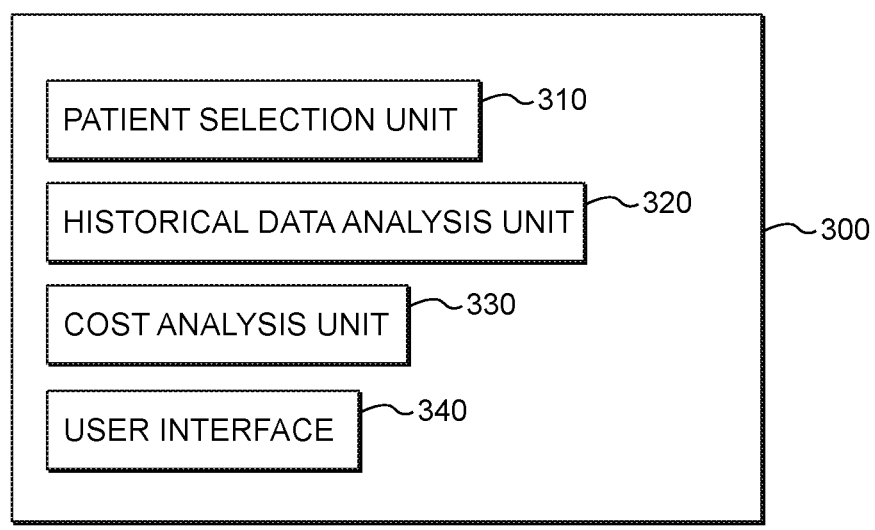
FIG. 7 is an illustrative block diagram of a value of future adherence engine.

FIG. 7 is an illustrative block diagram of a value of future adherence engine 300. As explained above, the value of future adherence engine 300 can receive a probability score for each patient from the prediction engine 200 in which the value of future adherence engine 300 generates a score associated with the value related to recommending intervention for a particular patient. The value of future adherence engine 300 can have a patient selection unit 310 which is used to select one or more patients for analysis and a historical data analysis unit 320 which is capable of applying historical/medical data of a patient in the cost reduction analysis. The engine 300 can also have a cost analysis unit 330 which can use the data from the historical data analysis unit 320 in determining the cost of adherence, non-adherence, and cost reduction for each patient as well as the probability of the patient converting from non-adherence to adherence. These factors can be used by the cost analysis unit 330 to generate the overall VFA score for a particular patient.

The engine 300 can also be configured to have a user interface 340 allowing one or more users to manipulate and view the data. An example user interface is shown in FIGS. 1 and 2.

Figure 8:
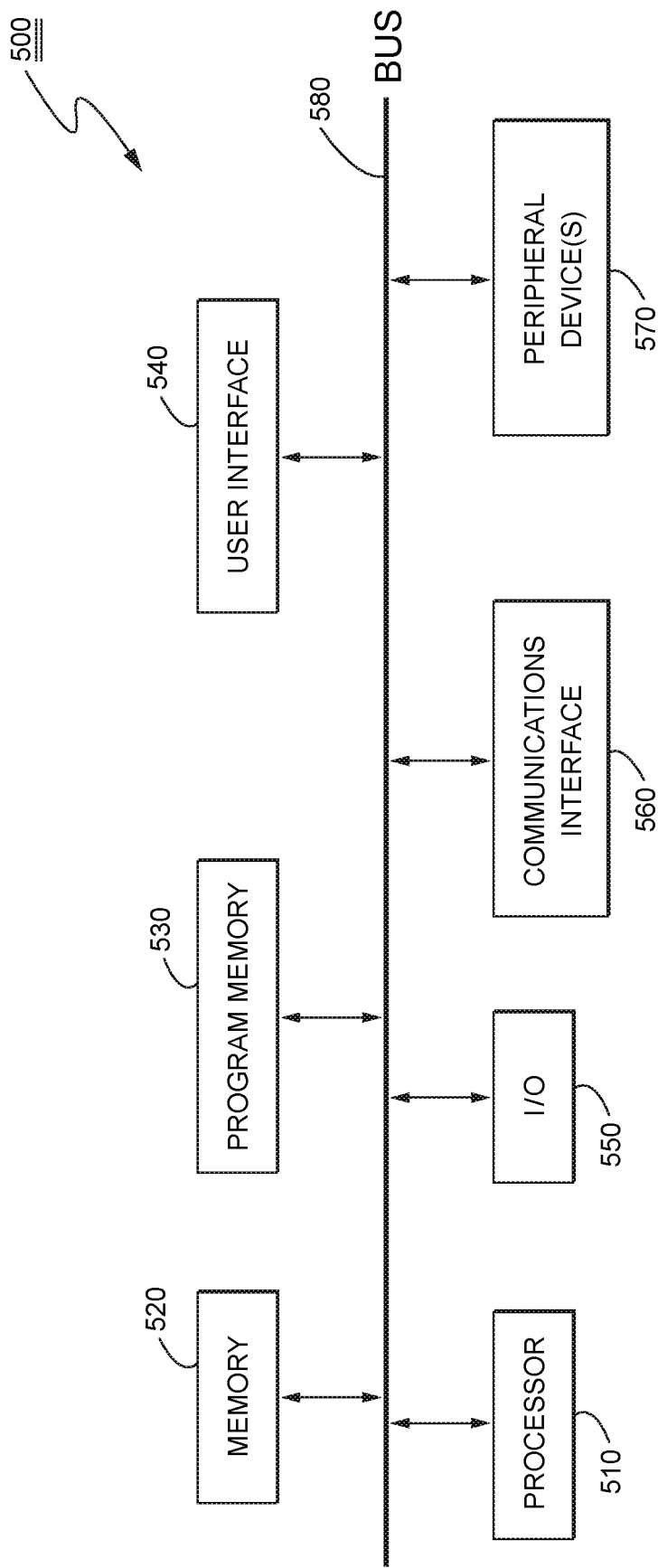
FIG. 8 shows an illustrative schematic block diagram of elements of a computing system that may be used to perform functions associated with an example embodiment.

FIG. 8 shows an illustrative schematic block diagram of elements of a computing system that may be used to perform functions associated with an example embodiment, which illustrates the basic requirements of such a computer system 500. In FIG. 8, a bus 580 interconnects a processor 510 with various hardware, firmware and software elements including, for example a memory 520 which may be used to store historical and candidate patient data as well as patient-specific patient-level data generated by the example health care management system described herein. Moreover, it will be understood that this memory is not necessarily integrated with the computing system 500, but may be operatively coupled to the system in any manner, including, for example, via a secured cloud, dedicated links, the Internet, or the like.

The computer system 500 may also include a program memory 530 containing various instructions or application software that may be used to operate the processor 510 and to process data, including, for example, machine-level code to run the basic operations of the processor as well as software for implementing the illustrated health care management system. It will be noted that the program memory 530 may also be integrated in whole or in part with the processor 510 and is not necessarily a separate element as shown in the drawings. The computer system 500 may further include several interfaces that enable various interactions with the system 500. For example, a user interface 540 is provided that allows operators to program the system 500 as well as to enter and manipulate data, and to extract information that may be stored in the memory 520 or other databases connected to the system 500. The user interface 540 may be, for example, in the form of a display and associated input/output devices, such as, for example, a keyboard, mouse, gesture pad, or the like (not shown).

The system 500 may also include a communications interface 560 that provides connections for allowing the system 500 to receive and transmit information to and from external sources via various communications links, including, for example, the Internet, an electronic health records system, dedicated links, secure clouds, or the like. For example, the communications interface 560 may be used to receive historical patient data and candidate patient data or patient-level files generated at another system or site. It is also contemplated that the system 500 may include peripheral devices 570, such as, for example, external memory, a printer, etc. While an example general computing system 500 has been described herein, it will be appreciated that those skilled in the art would be able to devise any suitable computing system to achieve the objects and features described herein with respect to the disclosed example health care management system.

As described above, the technology aims to achieve increased patient adherence to selected medication regimens and improvements in other quality and efficiency measures in defined patient populations. The technical field is health care and health care data analytics. The technology helps facilitate efficient population-level improvements in medication adherence and other health care outcomes. The technology leverages the use of patient-level predictions about future health care outcomes to inform the design and delivery of patient engagement activities.

The technology establishes the basis for innovative, prediction-driven performance improvement programs in health care that have the potential to improve the prevalence and performance of health care financial bonus programs for health care professionals designed to achieve targeted improvements in health care outcomes, including medication adherence commensurate with the value that those very targeted improvements create to sponsors of such programs. The technology constitutes the core enabler of new products that support health care improvement programs using financial incentives to encourage new and/or better informed actions by health care professionals to engage patients in new ways, including in taking their medications consistently as prescribed.

It should be appreciated that the VFA score for each patient is not limited to a single therapy and envisions covering multiple therapies. Likewise, the VFA score may be assigned to each patient for each therapy and the VFA scores may be combined to create a total score (i.e., showing the population score/value). Also, the VFA scores may be combined for a practice showing the overall VFA score for the total patient population in the practice.

It should also be appreciated that the source for the medical history data may come from a variety of resources including, but not limited to, medical claims data, pharmacy data, and/or survey data. The system is also configured so that the cost component of the VFA score is maximized while limiting the number of variables needed from pharmacy data when creating the cost table (i.e., no medical claims used in the cost table). Of course, these advantages are non-limiting and the system provides a number of different advantages over the conventional technology.

For purposes of explanation and non-limitation, specific details are set forth, such as particular nodes, functional entities, techniques, protocols, standards, etc. in order to provide an understanding of the described technology. It will be apparent to one skilled in the art that other embodiments may be practiced apart from the specific details described below. In other instances, detailed descriptions of well-known methods, devices, techniques, etc. are omitted so as not to obscure the description with unnecessary detail. Individual function blocks are shown in the figures. Those skilled in the art will appreciate that the functions of those blocks may be implemented using individual hardware circuits, using software programs and data in conjunction with a suitably programmed microprocessor or computer, using applications specific integrated circuitry (ASIC), and/or using one or more digital signal processors (DSPs). The software program instructions and data may be stored on computer-readable storage medium and when the instructions are executed by a computer or other suitable processor control, the computer or processor performs the functions. Although databases may be depicted as tables below, other formats (including relational databases, object-based models, and/or distributed databases) may be used to store and manipulate data.

Although process steps, algorithms or the like may be described or claimed in a particular sequential order, such processes may be configured to work in different orders. In other words, any sequence or order of steps that may be explicitly described or claimed does not necessarily indicate a requirement that the steps be performed in that order. The steps of processes described herein may be performed in any order possible. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the technology, and does not imply that the illustrated process is preferred.

Various forms of computer readable media/transmissions may be involved in carrying data (e.g., sequences of instructions) to a processor. For example, data may be (i) delivered from RAM to a processor; (ii) carried over any type of transmission medium (e.g., wire, wireless, optical, etc.); (iii) formatted and/or transmitted according to numerous formats, standards or protocols, such as Ethernet (or IEEE 802.3), SAP, ATP, Bluetooth, and TCP/IP, TDMA, CDMA, 3G, etc.; and/or (iv) encrypted to ensure privacy or prevent fraud in any of a variety of ways well known in the art.

While the technology has been described in connection with what is presently considered to be the most practical and preferred embodiment, it is to be understood that the technology is not to be limited to the disclosed embodiment, but on the contrary, is intended to cover various modifications and equivalent arrangements.

The invention claimed is:

1. A system, comprising:
   a processor; and
   a memory configured to store computer readable instructions that, when executed by the processor, cause the system to:
   generate a list of candidates using, at least, medical history data;
   calculate one or more values associated with medication adherence for each candidate in the list of candidates, wherein calculating the one or more values includes:
     determining a probability of non-adherence for each candidate in the list of candidates,
     determining a probability of conversion from non-adherence to adherence for each candidate in the list of candidates, and
     determining a cost reduction for each candidate, in the list of candidates, when the candidate is considered to be adherent;
   calculate a score for each candidate by combining the probability of non-adherence, for each candidate, by the probability of conversion from non-adherence to adherence, for each candidate, and further combining the cost reduction for each candidate when the candidate is considered to be adherent;
   apply the calculated score to each candidate; and
   generate a user interface for display that includes, at least, an ordered listing of each candidate, where each candidate in the ordered listing is displayed in association with an indication of medication adherence and a value associated with the score and corresponding to possible future adherence to at least one medication for each candidate.

2. The system of claim 1, wherein the system is further configured to:
   obtain data packets including, at least, the medical history data including one or more prescription drugs associated with the one or more candidates; and
   create a resultant data file using the medical history data for the one or more patients.

3. The system of claim 1, wherein the indication of medication adherence, included in the user interface generated for display, provides an indication of at least one health condition related to the candidate and a number of days that have passed between a current date and a date that a prescription related to the health condition should have been refilled.

4. The system of claim 3, wherein the indication of medication adherence, included in the user interface generated for display, provides an alert indicating that the prescription should be refilled.

5. The system of claim 1, wherein each candidate in the ordered listing is further displayed with a cost associated with intervention in addition to the displayed value.

6. The system of claim 1, wherein the system is further configured to:
   determine one or more interventions available for each candidate;
   assign a cost of each intervention of the one or more interventions available for each candidate; and
   enable selection of a cost effective intervention by comparing at least the calculated score to the cost of each intervention.

7. The system of claim 1, wherein the system is further configured to:
   determine a budget for participating in the one or more interventions; and
   modify the budget when an intervention in the one or more interventions is selected for a candidate.

8. The system of claim 1, wherein determining the probability of non-adherence for each candidate includes:
   identifying pharmacy claims for each candidate over a time period;
   computing variables related to therapies and/or demographic information for each candidate; and
   applying the computed variables and the pharmacy claims to a predictive model to generate the probability of non-adherence.

9. The system of claim 1, wherein determining the probability of conversion from non-adherence to adherence for each candidate includes:
   identifying pharmacy claims for each candidate over a time period;
   creating a profile for each candidate based on characteristics determined from evaluation experience associated with the respective candidate; and
   assigning a conversion rate to each candidate in the associated profile of the candidate and looking-up the conversion rate using the associated profile.

10. The system of claim 1, wherein determining the cost reduction for each candidate includes:
    identifying pharmacy claims for each candidate over a time period;
    creating or updating a profile for each candidate based on specified research and modeling factors; and
    assign the cost reduction to each candidate based on information associated with the profile of the candidate.

11. A method for determining a value of future adherence, comprising:
    at an information processing system having at least a processor and a memory:
    generating a list of candidates using, at least, medical history data;
    calculating one or more values associated with medication adherence for each candidate in the list of candidates, wherein calculating the one or more values includes:
    determining a probability of non-adherence for each candidate in the list of candidates, determining a probability of conversion from non-adherence to adherence for each candidate in the list of candidates, and determining a cost reduction for each candidate, in the list of candidates, when the candidate is considered to be adherent;

calculating a score for each candidate based on, at least, (a) the probability of non-adherence, for each candidate, (b) the probability of conversion from non-adherence to adherence, for each candidate, and (c) the cost reduction for each candidate when the candidate is considered to be adherent;

applying the calculated score to each candidate; and generating a user interface for display that includes, at least, a listing of each candidate, where each candidate in the listing is displayed in association with a value corresponding to the score and corresponding to possible future adherence to at least one medication for each candidate.

12. The method of claim 11, wherein the user interface further includes an indication of medication adherence displayed in association with each candidate.

13. The method of claim 12, wherein the indication of medication adherence, included in the user interface generated for display, provides an indication of at least one health condition related to the candidate and a number of days that have passed between a current date and a date that a prescription related to the health condition should have been refilled.

14. The method of claim 13, wherein the indication of medication adherence, included in the user interface generated for display, provides an alert indicating that the prescription should be refilled.

15. The method of claim 11, wherein each candidate in the listing is further displayed with a cost associated with intervention in addition to the displayed value.

16. A system, comprising:

a processor;

a communications interface; and a memory configured to store computer readable instructions that, when executed by the processor, cause the system to:

obtain medical history data from one or more information processing devices;

generate a list of candidates using, at least, the medical history data;

calculate values associated with medication adherence for each candidate in the list of candidates, wherein calculating the values includes:

determining a probability of non-adherence for each candidate in the list of candidates, determining a probability of conversion from non-adherence to adherence for each candidate in the list of candidates, and determining a cost reduction for each candidate, in the list of candidates, when the candidate is considered to be adherent;

calculate a score for each candidate based on the calculated values associated with medication adherence;

apply the calculated score to each candidate; and generate a user interface for display that includes one or more patients and values associated with the calculated score.

17. The system of claim 16, wherein the score for each candidate is calculated by combining the probability of non-adherence, for each candidate, by the probability of conversion from non-adherence to adherence, for each candidate, and further combining the cost reduction for each candidate when the candidate is considered to be adherent.

18. The system of claim 16, wherein the user interface further includes a listing of each candidate, where each candidate in the listing is displayed in association with a value corresponding to the score and corresponding to possible future adherence to at least one medication for each candidate.

19. The system of claim 18, wherein the user interface further includes an indication of medication adherence displayed in association with each candidate.

20. The system of claim 19, wherein the indication of medication adherence, included in the user interface generated for display, provides an indication of at least one health condition related to the candidate and a number of days that have passed between a current date and a date that a prescription related to the health condition should have been refilled.

* * * * *